United States Patent [19]

Forte et al.

[11] Patent Number: 5,011,496
[45] Date of Patent: * Apr. 30, 1991

[54] PROSTHETIC JOINT

[75] Inventors: Mark R. Forte, Pine Brook, N.J.; Douglas G. Noiles, New Canaan, Conn.

[73] Assignee: Joint Medical Products Corporation, Stamford, Conn.

[*] Notice: The portion of the term of this patent subsequent to Dec. 19, 2006 has been disclaimed.

[21] Appl. No.: 384,264

[22] Filed: Jul. 24, 1989

Related U.S. Application Data

[63] Continuation of Ser. No. 151,429, Feb. 2, 1988, Pat. No. 4,888,021.

[51] Int. Cl.⁵ .............................. A61F 2/38; A61F 2/30
[52] U.S. Cl. ........................................ 623/20; 625/18
[58] Field of Search .............................. 623/16, 18, 20

[56] References Cited

U.S. PATENT DOCUMENTS

| | | | |
|---|---|---|---|
| 3,728,742 | 4/1973 | Averill | 3/1 |
| 3,813,700 | 6/1974 | Tavernetti | 3/1 |
| 3,840,905 | 10/1974 | Deane | 623/20 |
| 3,878,566 | 4/1975 | Bechtol | 623/20 |
| 3,945,053 | 3/1976 | Hillberry et al. | 623/20 |
| 3,964,106 | 6/1976 | Hutter, Jr. et al. | |
| 3,996,624 | 12/1976 | Noiles | 3/1.911 |
| 4,001,896 | 1/1977 | Arkangel | 623/20 X |
| 4,064,568 | 12/1977 | Grundei et al. | 623/20 |
| 4,094,017 | 6/1978 | Matthews et al. | 623/20 |
| 4,138,894 | 6/1979 | Worrell | 623/20 |
| 4,209,861 | 7/1980 | Walker et al. | 3/1.911 |
| 4,213,209 | 7/1980 | Insall | 3/1.911 |
| 4,217,666 | 8/1980 | Averill | 3/1.911 |
| 4,219,893 | 9/1980 | Noiles | 3/1.911 |
| 4,249,270 | 2/1981 | Bahler et al. | 623/20 |
| 4,262,368 | 4/1981 | Lacey | 623/20 |
| 4,298,992 | 11/1981 | Burstein et al. | 623/20 |
| 4,301,553 | 11/1981 | Noiles | 3/1.911 |
| 4,309,778 | 1/1982 | Buechel et al. | 3/1.911 |
| 4,340,978 | 7/1982 | Beuchel et al. | 3/1.911 |
| 4,353,135 | 10/1982 | Forte et al. | 623/20 |
| 4,470,158 | 9/1984 | Pappas et al. | 3/1.911 |
| 4,568,348 | 2/1986 | Johnson et al. | 623/20 |
| 4,634,444 | 1/1987 | Noiles | 623/20 |
| 4,714,472 | 12/1987 | Averill et al. | 623/20 |

FOREIGN PATENT DOCUMENTS

| | | |
|---|---|---|
| 2227090 | 12/1973 | Fed. Rep. of Germany . |
| 2501128 | 7/1976 | Fed. Rep. of Germany . |
| 2269324 | 1/1976 | France . |
| 2478462 | 9/1981 | France . |
| 1507309 | 4/1978 | United Kingdom . |

Primary Examiner—David J. Isabella
Attorney, Agent, or Firm—Maurice M. Klee

[57] ABSTRACT

A prosthetic knee joint is provided having an extended position, an intermediate position, and a flexed position. The motion of the joint includes a minor segment from the extended position to the intermediate position, and a major segment from the intermediate position to the flexed position. The center of pressure between the femoral component and the tibial component moves rearward on the tibia during the minor segment. During the major segment, the joint flexes about an axis of rotation with the bearing surfaces on the femoral and tibial components being in congruent engagement. The distal surface of the femoral component includes two rails for engagement with a patellar prosthesis. The contour of the rails is either a straight line or a concave curve to provide line contact between the rails and the patellar prosthesis. In certain embodiments, the patellar prosthesis has a saddle-shaped surface so that the prosthesis and each of the rails can make contact over an area extending along the length of the rail.

12 Claims, 4 Drawing Sheets

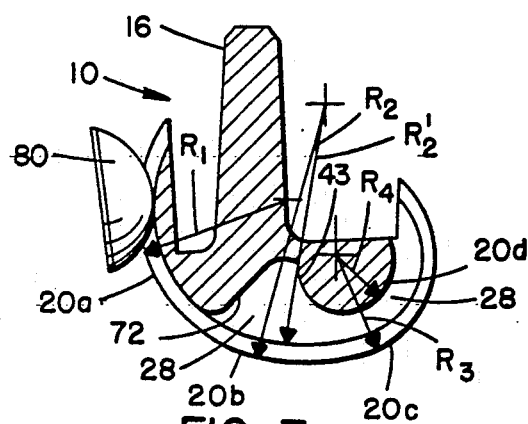
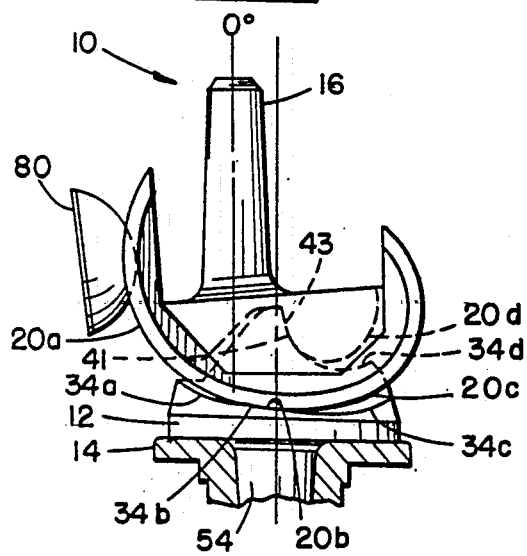
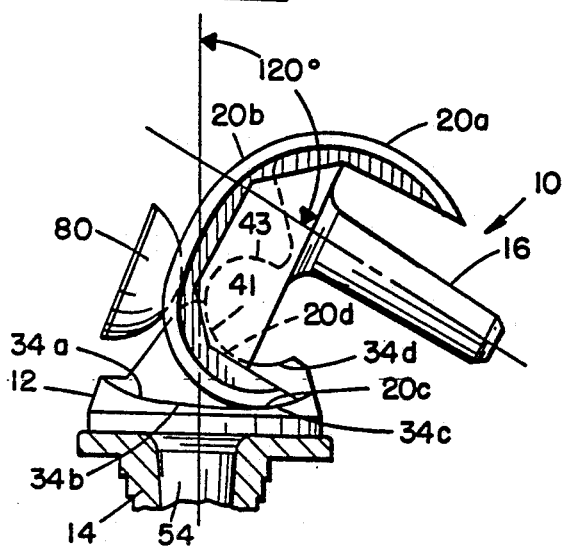
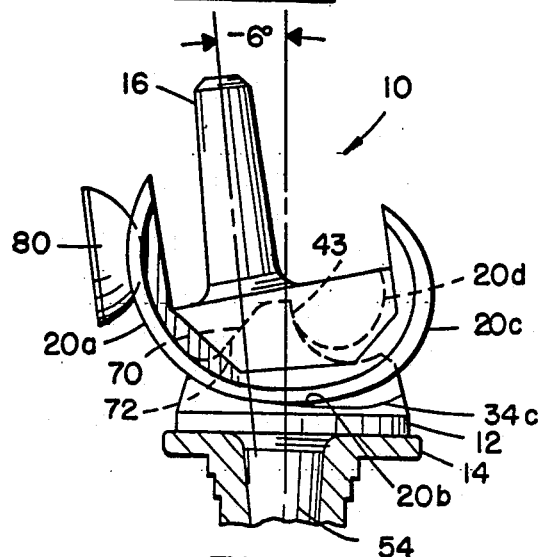
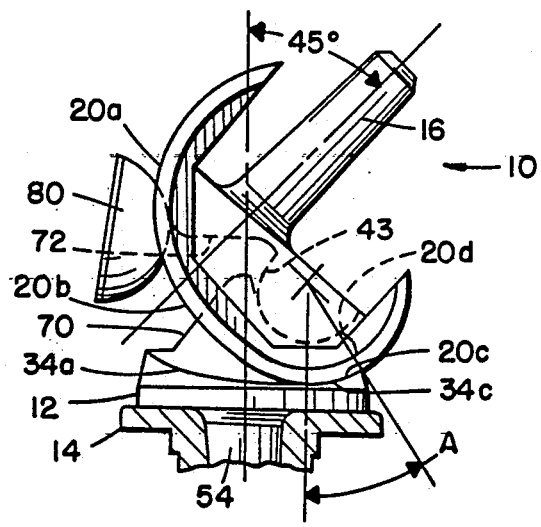
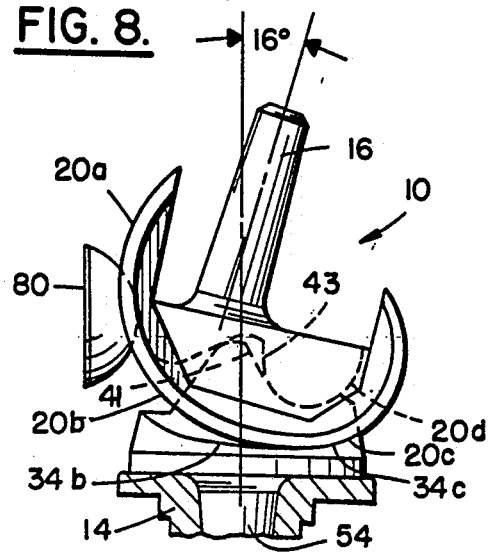

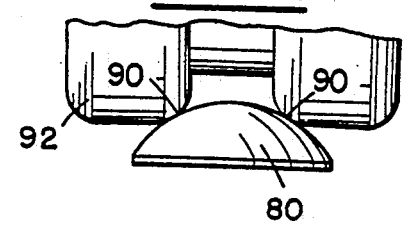
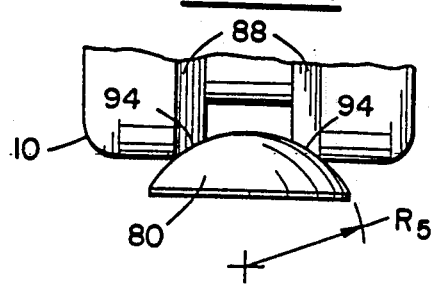
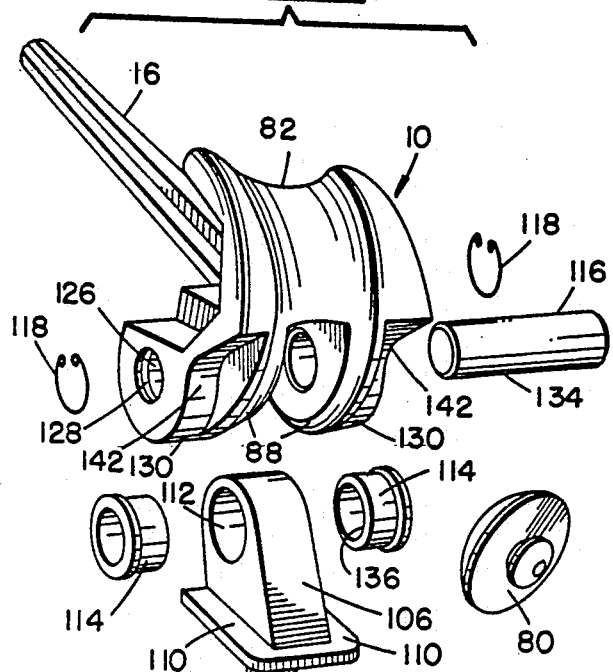
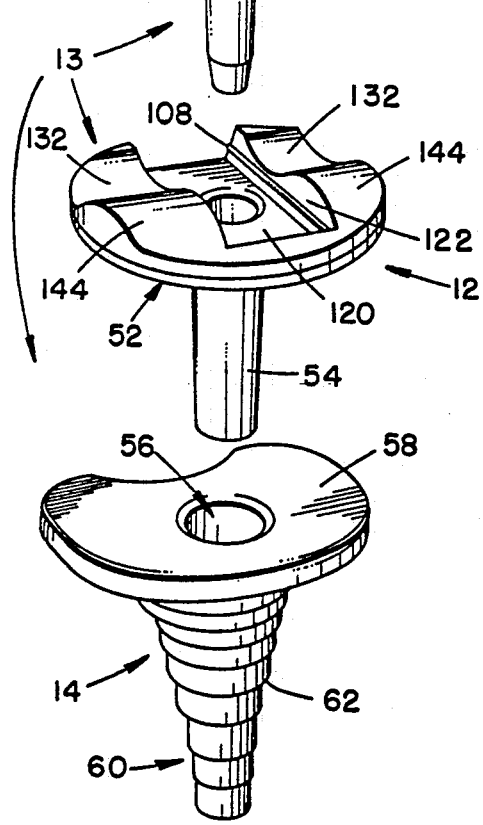
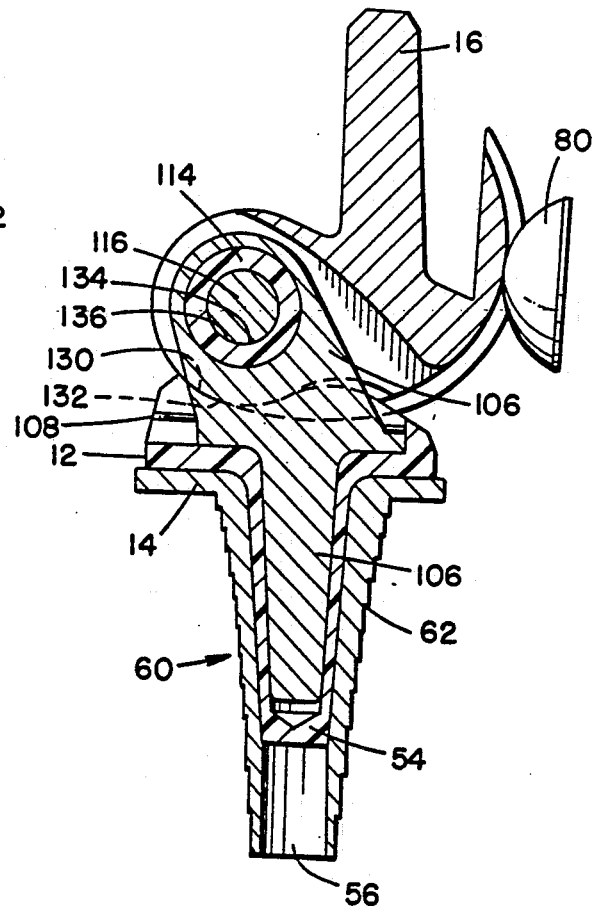

PROSTHETIC JOINT

This is a continuation of co-pending application Ser. No. 07/151,429, filed on Feb. 2, 1988 now U.S. Pat. No. 4,888,021.

BACKGROUND OF THE INVENTION

1. Field of the Invention

This invention relates to improved prosthetic joints and in particular to improved prosthetic knee joints.

2. Description of the Prior Art

Flexion and extension of the normal human knee involves complex movements of three bones: the femur, the tibia, and the patella. During flexion, the distal end of the femur and the proximal end of the tibia rotate and glide relative to one another, with the center of rotation of the joint moving posteriorly over the condyles of the femur; during extension, the tibia and femur follow the reverse path, with the center of rotation now moving anteriorly as the joint is extended. Simultaneous with these movements of the femur and tibia, the patella moves over the surface of the femoral condyles, while remaining at a relatively constant distance from the tubercle of the tibia through the attachment of the patella to the tibia by the patellar ligament.

Numerous prostheses have been proposed as replacements for the natural knee joint. See, for example, Noiles, U.S. Pat. Nos. 3,996,624, 4,219,893, and 4,301,553, Averill, U.S. Pat. Nos. 3,728,742 and 4,217,666, Insall, U.S. Pat. No. 4,213,209, Tavernetti, U.S. Pat. No. 3,813,700, German Patent Publications Nos. 2,227,090 and 2,501,128, and French Patent Publications Nos. 2,269,324 and 2,478,462. For total knee replacements, the condyles of the femur and the head of the tibia are surgically removed and replaced with prosthesis components. A patellar prosthesis, e.g., a spherically-domed or conical plastic button, is normally attached to the posterior surface of the patella to serve as an interface between the patella bone and the femoral prosthesis.

Efforts have been made to produce prosthetic joints which function in a manner similar to the natural knee. Specifically, a number of mechanisms have been proposed for producing posterior movement of the femoral component relative to the tibial component (femoral roll-back on the tibia) as the joint is flexed. For example, Walker et al., U.S. Pat. No. 4,209,861, discloses a prosthetic knee joint wherein guiding surfaces on the femoral and tibial components are used to induce posterior movement on the tibial component of the contact area between the components as the knee is progressively flexed. The posterior movement takes place through a major portion of the flexion of the joint. Burstein et al., U.S. Pat. No. 4,298,992, shows an alternate construction in which the femoral component moves posteriorly relative to the tibial component at or near full flexion. See also Deane, U.S. Pat. No. 3,840,905.

These prior art constructions suffer the common disadvantage that the femoral and tibial bearing surfaces are only in contact over small areas. Moreover, the contact areas become even smaller when the joint is flexed. During flexion, e.g., during such activities as squatting, stair climbing, or rising from a chair, high loads are applied to the joint and must be carried by the contact area between the bearing surfaces. Small contact areas plus high loads lead to high rates of wear of the bearing surfaces, which is clearly undesirable.

U.S. Pat. No. 4,634,444 to Douglas G. Noiles discloses a knee joint having bearing surfaces of large areas. However, the femoral component of this joint does not move posteriorly relative to the tibial component during flexion, as occurs in the natural knee.

Efforts have also been made to improve the functioning of patellar prostheses. See, for example Pappas et al., U.S. Pat. No. 4,470,158, Buechel et al., U.S. Pat. No. 4,309,778, and Buechel et al., U.S. Pat. No. 4,340,978. In particular, the anterior surfaces of femoral components have been provided with concave recesses for receiving patellar prostheses when the joint is at or near its fully extended position. See, for example, Forte et al., U.S. Pat. No. 4,353,135, and Walker, U.S. Pat. No. 4,209,861. Similarly, the distal surfaces of femoral components have included tracks for receiving the patellar prosthesis when the joint is flexed. Significantly, the surfaces which engage the patellar prosthesis on these prior art tracks have been convexly shaped. Indeed, discontinuities in the slope of the prosthesis' outer surface have existed at the intersection between the concave recess of the anterior surface and the convex track of the distal surface.

Prostheses employing convex tracks have suffered a number of disadvantages. When used with the typical spherically-domed or conical patellar prosthesis, the track and the patellar prosthesis have only made point contact. As discussed above, prosthetic knee joints are subject to high loads when flexed, i.e., when the patellar prosthesis is in contact with the distal track. This combination of high loads and point contact has resulted in high wear rates for the patellar prosthesis. Indeed, for patellar prostheses consisting of a plastic bearing mounted on a metal backing plate, complete wear through of the bearing so as to cause the metal plate and the metal femoral component to grind against one another in situ, has been observed.

In addition to the point contact problem, the discontinuity in the outer surface of the femoral prosthesis at the intersection between the concave recess and the convex track has also contributed to wearing of the patellar prosthesis and has degraded the overall smooth operation of the prosthesis.

The Forte et al. patent referred to above discloses a construction for a patellar prosthesis which can achieve line contact with a convex track. This construction, however, employs a complex patellar button geometry which must be precisely aligned with the femoral prosthesis during the surgical procedure for the system to operate properly. Also, in revision surgery, the existing patellar prosthesis is normally not replaced. Most existing patellar prostheses are of the conical or spherically-domed button type. The Forte et al. construction, like the rest of the prior art constructions, only provides point contact when used with such spherically-domed or conical patellar prostheses.

SUMMARY OF THE INVENTION

In view of the foregoing state of the art, it is an object of the present invention to provide improved prosthetic joints and in particular improved prosthetic knee joints.

More particularly, one of the objects of the invention is to provide a prosthetic joint composed of two components, e.g., a femoral component and a tibial component, wherein the first component translates relative to the second component as the joint moves from its extended to its flexed position and wherein the area of contact between the bearing surfaces of the first and second components is large, and, in particular, is large when the joint is flexed. Another object of the invention, is to provide a femoral prosthesis whose distal surface is configured to provide line contact, as opposed to point contact, with a patellar prosthesis, including line contact with the spherically-domed and conical button-type prostheses which are typically encountered in revision surgery.

To achieve the foregoing and other objects, the invention in accordance with certain of its aspects provides an artificial joint which has an extended position, an intermediate position, and a flexed position. The motion of the joint includes a minor segment and a major segment, the minor segment comprising movement between the extended and the intermediate positions, and the major segment comprising movement between the intermediate and the flexed positions.

The joint comprises two components, e.g., for a knee prosthesis, the femoral component and the tibial component. Each component includes a bearing surface and a cam member. Each bearing surface includes a first portion and a second portion, the first portions being in engagement with one another during the minor segment of the joint's motion, and the second portions being in engagement with one another during the major segment of the joint's motion. In certain preferred embodiments, the second portions comprise large area, stepped bearing surfaces of the type disclosed in U.S. Pat. No. 4,634,444, referred to above, the pertinent portions of which are incorporated herein by reference.

During the major segment of the joint's motion, the motion of the joint comprises rotation about an axis of flexion. The rotation takes place through sliding of the bearing surfaces of the second portions relative to one another. The cam members on the first and second components interact with one another during the minor segment of the joint's motion. In particular, the cam members permit the first portions of the bearing surfaces to roll relative to one another as the joint moves between its extended and intermediate positions.

In a preferred construction of the joint, the area of contact between the second portions of the bearing surfaces is greater than the area of contact between the first portions. This construction maximizes the operational bearing contact area of the joint since, as discussed above, the second bearing surfaces are in contact during the major segment of the joint's motion. Moreover, for knee joints, this construction provides a large area of contact during flexion of the joint, i.e., during times when the joint is subject to high loading forces.

In accordance with other aspects of the invention, a femoral prosthesis is provided whose outer surface has an anterior portion and a distal portion. The anterior portion includes a recess for engagement with a patellar prosthesis, and the distal portion includes a track for the same purpose. The track is composed of two rails which intersect the recess. The surface of each of the rails has a cross-sectional contour in a direction transverse to the longitudinal axis of the rail which is (1) either a straight line or a concave curve, (2) constant along the length of the rail, and (3) matches the contour of the surface of the recess at the intersection between the rail and the recess.

By means of this structure, the patellar prosthesis moves smoothly over both the anterior and distal surfaces of the femoral prosthesis, including the transition between those surfaces. Moreover, the patellar prosthesis makes line contact with the distal surface of the femoral prosthesis. In particular, when the contour of the rails is a portion of a straight line, line contact with conical patellar buttons is achieved, and when the contour of the rails is a portion of a concave circle, line contact with spherically-domed patellar buttons is achieved.

The accompanying drawings, which are incorporated in and constitute part of the specification, illustrate the preferred embodiments of the invention, and together with the description, serve to explain the principles of the invention. It is to be understood, of course, that both the drawings and the description are explanatory only and are not restrictive of the invention. In particular, it is to be understood that although, for ease of discussion, the description which appears below is in terms of an artificial knee joint, various aspects of the invention are equally applicable to other types of artificial joints, such as, artificial elbow joints and the like.

BRIEF DESCRIPTION OF THE DRAWINGS

FIG. 6 is a cross-sectional view along lines 6—6 in FIG. 4.

FIGS. 7–10 are side views of the joint of FIG. 1 at flexion angles of 0°, 16°, 45°, and 120°, respectively.

FIG. 11 is a side view of the joint of FIG. 1 at a hyperextended angle of −6°.

FIGS. 12 and 13 compare the engagement between the patellar and femoral components achieved with the present invention (FIG. 13) with that achieved with prior art prostheses (FIG. 12).

FIG. 14 is a perspective, exploded view of a constrained artificial knee joint employing the patella tracking system of the present invention.

FIG. 15 is a cross-sectional view of the joint of FIG. 14 along the midline of the prosthesis.

DESCRIPTION OF THE PREFERRED EMBODIMENTS

Figure 1:
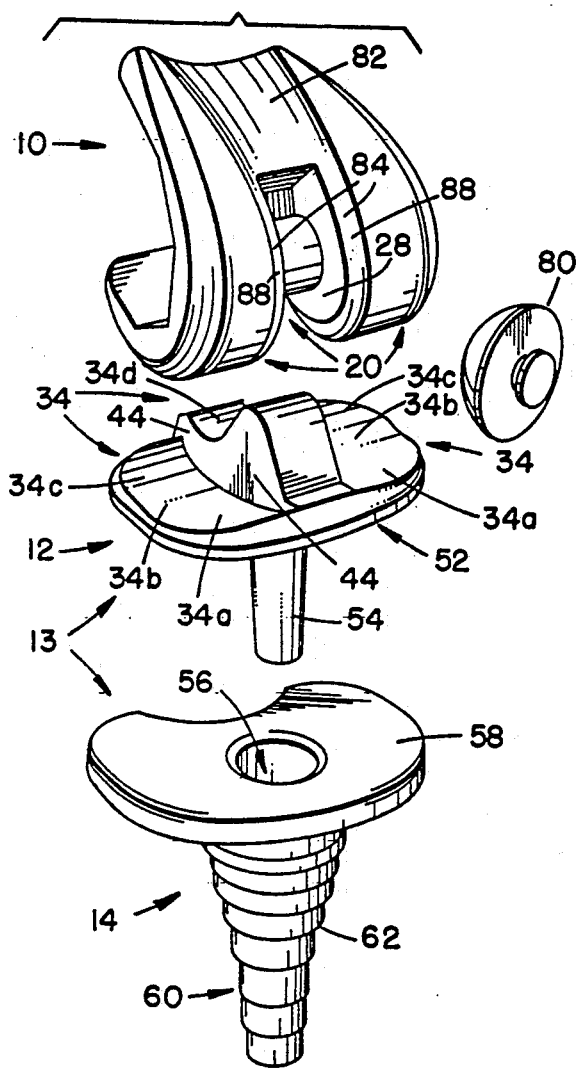
FIG. 1 is a perspective, exploded view of a semi-constrained artificial knee joint constructed in accordance with the present invention.

Referring now to the figures, there is shown in FIG. 1 an exploded view of a semi-constrained artificial knee joint constructed in accordance with the present invention. The joint includes a femoral component 10 and a tibial component 13 comprising tibial plateau component 12 and tibial sleeve component 14. As discussed in detail below, the joint is designed to smoothly interact with patellar prosthesis 80.

Femoral component 10 and tibial plateau component 12 respectively carry mating convex bearing surface 20 and concave bearing surface 34 (see FIG. 1). As shown in FIG. 6, femoral convex bearing surface 20 is composed of part 20a described by radius $R_1$, part 20b described by radius $R_2$, and part 20c described by radius $R_3$. Femoral convex surface 20 also includes part 20d described by radius $R_4$. Radius $R_4$ has the same center as radius $R_3$, and therefore surface 20d is concentric with surface 20c. Part 20b is also referred to herein as the first portion of convex bearing surface 20; the combination of parts 20c and 20d are also referred to herein as the second portion of convex bearing surface 20.

Figure 2:
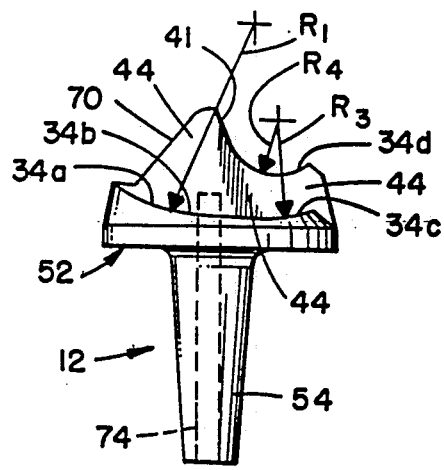
FIG. 2 is a side view of the tibial plateau component of the joint of FIG. 1.
Figure 3:
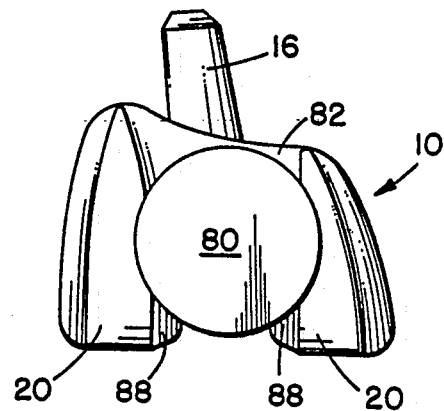
FIG. 3 is a view of the anterior surface of the femoral component of the joint of FIG. 1 showing the engagement of the patellar component of the joint of FIG. 1 with the anterior surface.

As shown in FIG. 2, tibial concave bearing surface 34 is composed of part 34a described by radius $R_1$, part 34b which may be flat or concave with a radius greater than radius $R_2$ of femoral component 10, and part 34c described by radius $R_3$. Tibial concave surface 34 also includes part 34d described by radius $R_4$. Radius $R_4$ has the same center as radius $R_3$, and therefore surface 34d is concentric with surface 34c. Part 34b is also referred to herein as the first portion of concave bearing surface 34; the combination of parts 34c and 34d are also referred to herein as the second portion of concave bearing surface 34.

Figure 5:
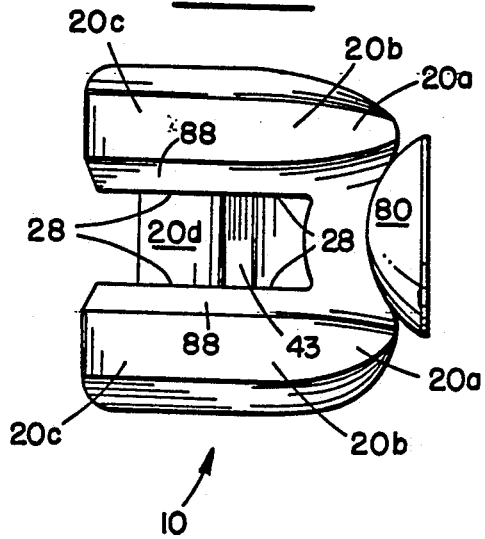
FIG. 5 is a view of the distal surface of the femoral component of the joint of FIG. 1 showing the engagement of the patellar component with the anterior surface.
Figure 16:
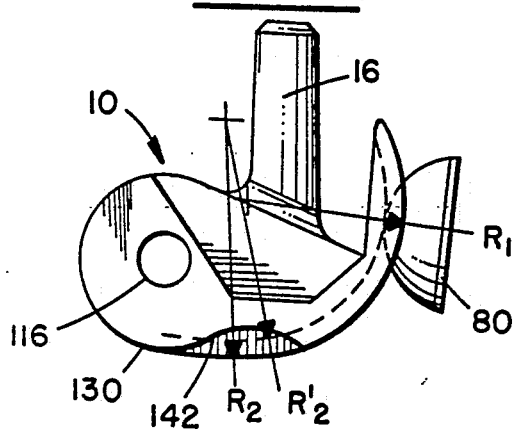
FIG. 16 is a side view of the femoral and patellar components of the joint of FIG. 14.
Figure 17:
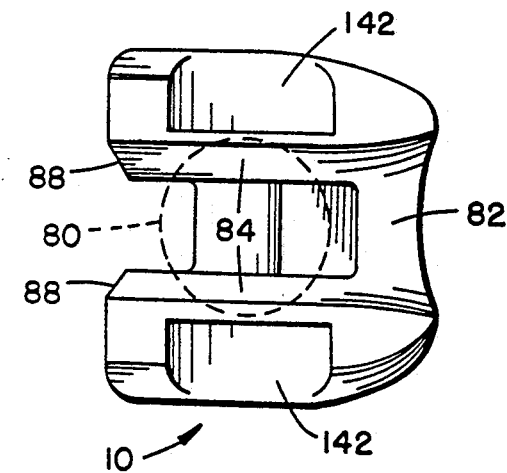
FIG. 17 is a view of the distal surface of the femoral component of the joint of FIG. 14 showing the engagement of the patellar component with the distal surface.

As shown in FIGS. 1 and 5, each of parts 20a, 20b, and 20c, and parts 34a, 34b, and 34c are composed of two spaced-apart sections. The spaced-apart sections of parts 20c and 34c, in combination with parts 20d and 34d, respectively, form stepped bearings of the type disclosed in U.S. Pat. No. 4,634,444, referred to above. As shown in the figures, these stepped bearings extend across the full width of the prosthesis so as to provide a large, wear-resistant bearing surface for flexion motions of the joint. Preferably, parts 20c and 20d, i.e., the second portion of convex bearing surface 20, and parts 34c and 34d, i.e., the second portion of concave bearing surface 34, are surfaces of revolution, i.e., cylindrical in shape, although other bearing contours can be used in the practice of the invention.

So that the bearing surfaces can come apart in a direction orthogonal to their axis of rotation, the second portion of concave bearing surface 34 encompasses less than one-half of the second portion of convex bearing surface 20. In particular, as shown in FIG. 9, the second portions engage each other over an angle A, which for the embodiment shown is approximately 15°.

The spaced-apart sections of part 34c are connected to part 34d by walls 44. Similarly, the spaced-apart section of part 20c are connected to part 20d by walls 28. The presence of these walls stabilizes the assembled joint against dislocations along the axis of rotation of the second portions of bearings 20 and 34. Specifically, the engagement of the walls limits the lateral motion of surfaces 20 and 34 with respect to one another. Significantly, this stabilization is achieved without sacrificing the overall width of the bearing surfaces, as would occur with other modes of lateral stabilization known in the art, such as, through the use of a post or the like between two laterally separated bearing surfaces.

As shown in the figures, the outer sections of parts 20c and 34c have equal radii of curvature, and those radii of curvature are larger than the radius of curvature of parts 20d and 34d. It is to be understood that the bearing surfaces can have radii of curvature other than those shown, provided that the radii are such that their differences produce walls 28 and 44 of sufficient height to restrain the joint against lateral dislocations.

As can best be seen in FIG. 2, in addition to bearing surfaces 34, tibial plateau component 12 also includes cam means 41. Similarly, as can be seen in FIG. 6, femoral component 10 includes cam means 43. Cam means 41 is located between the spaced-apart sections of part 34b and comprises an extension of part 34d. Cam means 43 is located between the spaced-apart sections of part 20b and comprises an extension of part 20d. Cam means 41 is connected to part 34b by extensions of walls 44. Similarly, cam means 43 is connected to part 20b by extensions of walls 28. These extensions can also engage against one another to help restrain the joint at flexion angles against lateral dislocations.

The operation of cam means 41 and 43 is illustrated in FIGS. 7-10, where FIG. 7 shows the joint in its extended position, FIG. 8 shows the joint in its intermediate position, and FIGS. 9 and 10 show the joint at flexion angles of 45° and 120°, respectively.

As shown in these figures, parts 20b and 34b, i.e., the first portions of surfaces 20 and 34, are in engagement in the joint's extended position (FIG. 7) and roll relative to one another as the joint moves from its extended position to its intermediate position (FIG. 8). The theoretical contact between parts 20b and 34b during this rolling is line contact. Cam means 41 and 43 interact during this portion of the joint's motion to allow and control the rolling between the bearing surfaces. The natural forces in the knee tend to keep the cam means in contact through the minor segment of the joint's motion.

Parts 20c and 34c, as well as parts 20d and 34d, come into engagement at the intermediate position and remain in engagement throughout the remainder of the flexion of the joint (FIGS. 9-10). The motion of the joint when these second portions of surfaces 20 and 34 are in engagement consists of simple rotation of the joint about the axis defined by the common center of radii $R_3$ and $R_4$. The second portions slide on one another during this rotation.

The transition from the engagement of the first portions, which, as discussed above, is theoretically just line contact, to the engagement of the second portions results in an increase in the contact area between the bearing surfaces. Specifically, the contact area increases because of the congruent meshing of part 20c with part 34c and part 20d with part 34d. Flexing beyond the intermediate position is accomplished with substantial bearing areas in contact to resist the high femur to tibia loads created by weight bearing at greater flexion angles. For the joint of FIG. 1, this congruent bearing area is on the order of 1.0 square inch.

To maximize the contact area between the bearing surfaces through the major segment of the motion of the joint, the transition between the first and second portions of the bearing surfaces is performed early in the flexion of the joint. In FIGS. 7-10, the transition takes place at a flexion angle of about 16° from the extended position of the joint. The motion of the joint thus consists of a minor segment from 0° to about 16°, and a major segment from about 16° to the flexed position of the joint, e.g., 100° to 120°, with the major segment being about 5 times greater than the minor segment.

The transition point between the first and second portions of the bearing surfaces can of course be set at flexion angles either greater than or less than 16°. In general, the transition point should occur at a flexion angle of less than about 30° in order to obtain the full benefits of the enhanced bearing surface contact area provided by the engagement of the second portions.

In addition to moving between its extended and flexed positions, the joint of FIG. 1 can also be hyperextended. The amount of hyperextension permitted is determined by the engagement of surface 72 on femoral component 10 (see FIG. 6) with surface 70 on tibial plateau 12 (see FIG. 2). Radius $R_1$ of femoral surface 20a also comes into contact with radius $R_1$ of tibial surface 34a which further inhibits hyperextension. FIG. 11 shows the joint in its fully hyperextended condition. For the joint shown, the hyperextension is limited to $-6°$. Greater or lesser amounts of hyperextension can be permitted as desired.

In addition to carrying convex bearing surface 20 and cam means 43, femoral component 10 also includes fixation shank 16 which is adapted to be implanted in the patient's femur using standard surgical techniques. Similarly, in addition to concave bearing surface 34 and cam means 41, tibial plateau component 12 also includes depending shaft 54 and thrust bearing surface 52. As shown in FIG. 2, depending shaft 54 can optionally include metal reinforcing rod 74.

In the assembled joint, bearing surface 52 on the bottom of tibial plateau component 12 mates with bearing surface 58, i.e., the top surface of tibial sleeve 14, and depending shaft 54 is received in aperture 56 formed in the body of the tibial sleeve. As fully described in U.S. Pat. Nos. 4,219,893 and 4,301,553, referred to above, the pertinent portions of which are incorporated herein by reference, this arrangement of these components allows tibial sleeve 14 to rotate with respect to tibial plateau component 12 as the femur and tibia move from a position of full extension to a position of flexion. This rotation of the tibia about its longitudinal axis during flexion is normally in the range of 10°-15°.

Tibial sleeve component 14 is designed to be implanted in the upper portion of the tibia. Various approaches can be employed for this implantation. One such approach is that described in PCT Patent Publication No. W085/03426, entitled "Apparatus for Affixing a Prosthesis to Bone," which is assigned to the same assignee as this application. Briefly, this technique involves providing tibial sleeve 14 with an outer surface 60 which has been contoured to mate with a portion of the inner surface of the hard bone at the upper end of the tibia. In addition to being anatomically contoured, the surface is also provided with a geometry 62 designed to transform wedging shear loading to compression loading in the tibial bone. A further discussion of the technique can be found in the above-referenced patent publication, the pertinent portions of which are incorporated herein by reference.

In addition to engaging tibial component 13, femoral component 10 also engages patellar prosthesis 80. For this purpose, the anterior surface of the femoral component includes concave recess 82 and the distal surface includes track 84 which intersects the recess. Track 84 is composed of rails 88, each of which has a cross-sectional contour in a direction transverse to the longitudinal axis of the rail which is (1) either a straight line or a concave curve, (2) constant along the length of the rail, and (3) matches the contour of the surface of recess 82 at the intersection between the rail and the recess.

The advantage of constructing rails 88 in accordance with the invention is illustrated in FIGS. 12 and 13. FIG. 12 shows the construction used in the prior art wherein the portion of the distal surface of femoral prosthesis 92 which engaged patellar prosthesis 80 is convexly shaped. As shown in this figure, the two prostheses only make point contact at points 90. Such point contact leads to high wear rates for the patellar prosthesis. Also, in such prior art prostheses, distinct slope changes exist at the intersection between the convex surface and the concave recess formed in the prosthesis' anterior surface for receiving the patellar prosthesis.

Figure 4:
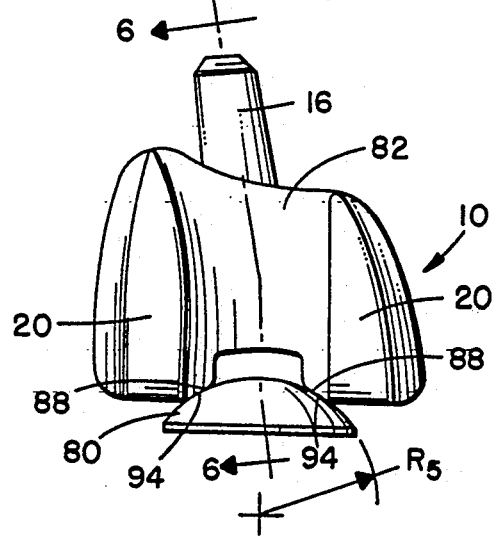
FIG. 4 is a view of the anterior surface of the femoral component of the joint of FIG. 1 showing the engagement of the patellar component with the distal surface of the femoral component.

In contrast to FIG. 12, as shown in FIG. 13, when rails 88 are given the configuration of the present invention, line contact along curves 94 is achieved between the patellar and femoral prostheses. As shown in FIG. 4, to achieve this line contact for a spherically-domed patellar button, curves 94 are portions of a circle having the same radius of curvature $R_5$ as the domed surface of the patellar prosthesis. For typical prosthesis dimensions, each of curves 94 can have a length, which corresponds to the width of the rail, on the order of 5-6 millimeters.

The line contact between the patellar prosthesis and the distal surface of the femoral prosthesis results in substantially reduced wear rates in comparison to those achieved with point contact. Also, as can be seen in, for example, FIG. 1, the concave contour of rails 88 results in a completely smooth transition between the rails and concave recess 82.

In the case of a conical patellar button, rails 88 are portions of a straight line instead of being concave. In such a case, recess 82 would preferably be V-shaped, i.e., composed of two inwardly sloping planes, so as to produce a smooth transition between the rails and the recess.

Figure 18:
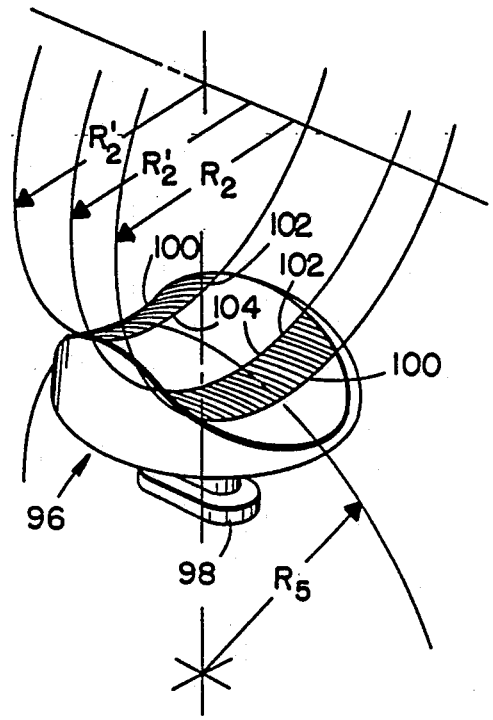
FIG. 18 is a perspective view of a patellar prosthesis having a saddle-shaped surface.

A patellar prosthesis 96 for use with the present invention which achieves even greater contact with the distal surface of the femoral prosthesis is shown in FIG. 18. The anterior surface of this prosthesis includes peg 98 for attaching the prosthesis to the posterior surface of the patient's patella. The posterior surface of the prosthesis, which engages the femoral prosthesis in the assembled joint, has a saddle shape.

As shown in FIG. 18, the saddle has a radius of curvature $R_5$ in the medial-lateral direction. This curvature matches the medial-lateral radius of curvature of rails 88 (see FIGS. 4 and 13), and thus contact like that achieved for a spherically-domed patellar prosthesis is achieved in this direction. Along lines 100 and 102, the saddle has radii of curvature of $R_2$ and $R_2'$, respectively. As can be seen in FIG. 6, $R_2$ is the radius of curvature of the outer edge of rails 88, while $R_2'$ is the radius of curvature of the inner edge of the rail. Accordingly, patellar prosthesis 96 will make surface contact throughout areas 104 with rails 88 of the femoral prosthesis when the patellar button is in contact with the $R_2$ section of track 84, which condition exists during the high contact forces created by flexion and weight bearing.

Figure 19:
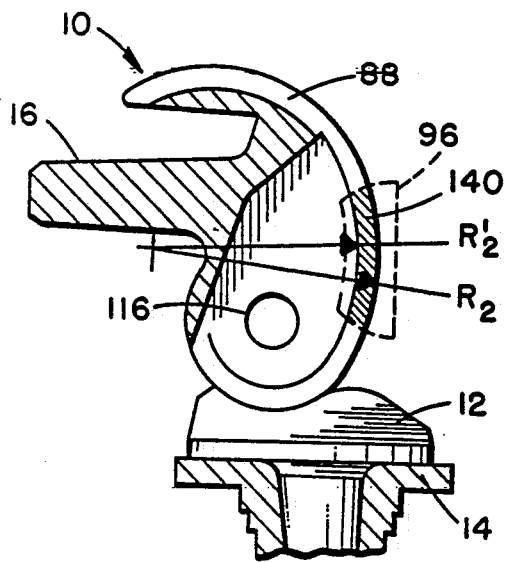
FIGS. 19 and 20 are sectional views in sagittal planes comparing the engagement of the femoral component of the joint of FIG. 14 with a spherically-domed patellar button (FIG. 20) and with the patellar prosthesis of FIG. 18 (FIG. 19).
Figure 20:
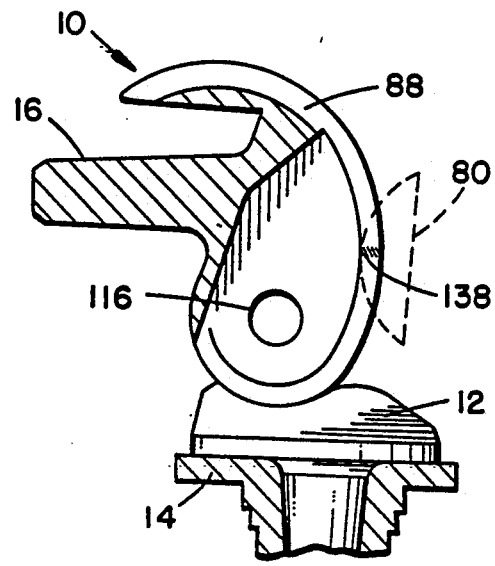

This enhanced contact is illustrated in the sectional views of FIGS. 19 and 20. As shown in FIG. 20, through the use of concave rails 88, a spherically-domed button is able to achieve line contact along line 138. However, as shown in FIG. 19, by using concave rails and a button having the saddle contour of FIG. 18, contact is achieved throughout area 140.

FIGS. 14-20 illustrate a constrained ("hinged") artificial knee joint employing concave rails 88 for engaging either spherically-domed patellar prosthesis 80 or saddle-shaped patellar prosthesis 96. For this prosthesis, tibial plateau 12 carries hinge post 106. For this purpose, the tibial plateau includes slot 120 having side walls 122. The hinge post is mounted to the tibial plateau by snapping flanges 110 under beads 108 formed in side walls 122.

Hinge post 106 includes hole 112 for receiving two flanged bearings 114, one from each side. The joint is assembled by slipping femoral component 10 over the hinge post to bring bearing surfaces 130 on the femoral component into contact with bearing surfaces 132 on the tibial plateau. Hinge pin 116 is then slid through holes 126 in the femoral component and through bearings 114 to assemble the hinge. Hinge pin 116 is held in place by means of snap rings 118 which are received in grooves 128.

As in the joint of FIGS. 1-11, the joint of FIGS. 14-20 has large bearing surfaces which extend across essentially the full width of the joint. Specifically, the bearing surfaces associated with the femoral side of the joint comprise surfaces 130 and lower outer surface 134 of hinge pin 116. The corresponding concentric bearings surfaces on the tibial side comprise surfaces 132 and the lower inner surface of bearings 114.

Hinge pin 116 and femoral component 10 are made from materials having similar wear characteristics, e.g., from titanium or cobalt chromium alloys. Similarly, bearings 114 and tibial plateau 12 are made from materials having similar wear characteristics, e.g., from ultra-high molecular weight polyethylene. In this way, the concentricity of the bearing surfaces is maintained as those surfaces wear since the wearable components, i.e., the plastic components, are all associated with one side of the joint, e.g., the tibial side, and are all surfaces of revolution about the same center line, while the non-wearable components, i.e., the metal components, are all associated with the other side of the joint, e.g., the femoral side, and are surfaces of revolution about the same center line as the plastic components. Accordingly, as the plastic components wear, the common center line will simply shift, e.g., move towards the tibia, with each of the metal and plastic bearing surfaces remaining concentric to its mating surface.

Bearing surfaces 130 are located further from the midplane of the joint than bearing surfaces typically used in hinged joints. This change allows rails 88 to be moved far enough apart to provide a stable engagement with the patellar prosthesis. During articulation of the joint, rails 88 ride inside of walls 122 and are received in slot 120. The outside surface of the femoral component 10 includes recesses 142 which engage protuberances 144 at the limit of the extension of the joint.

Femoral component 10, tibial component 13 and patellar components 80 and 96 can be made out of a variety of biologically compatible, surgically implantable materials. For example, a cobalt-chromium-molybdenum alloy, such as that described in ASTM F75, can be used for femoral component 10, a titanium-aluminum-vanadium alloy, such as that described in ASTM F136 can be used for tibial sleeve 14, and ultra-high molecular weight polyethylene (UHMWPE) can be used for tibial plateau component 12, bearings 114 and the patellar prostheses. Similarly, hinge post 106, hinge pin 116, and snap rings 118 can be made of cobalt-chrome or titanium alloys. Other types and combinations of materials appropriate for use in the artificial joint of the present invention will be evident to persons skilled in the art.

Although specific embodiments of the invention have been described and illustrated, it is to be understood that modifications can be made without departing from the invention's spirit and scope. For example, bearing surfaces have configurations other than those shown herein can be used in the practice of the invention. Similarly, a variety of cam means other than those described can be used to permit rolling of the bearing surfaces relative to each other during the minor segment of the joint's motion.

What is claimed is:

1. A prosthetic joint for providing flexion motion between two bones comprising:
   (a) a convex bearing component having a first bearing area and a contiguous second bearing area, the second bearing area being a surface of revolution about a first axis and having a radius of curvature which is less than the radius of curvature of the first bearing area; and
   (b) a concave bearing component having a third bearing area for engagement during flexion with the first bearing area and a contiguous fourth bearing area for engagement with the second bearing area, the fourth bearing area being a surface of revolution about a second axis and having a radius of curvature which is less than the radius of curvature of the third bearing area;

wherein:
   the radius of curvature of the second bearing area is substantially the same as the radius of curvature of the fourth bearing area so that the second and fourth bearing areas may be in congruent engagement with one another; and
   the flexion axis of the joint is parallel to the first and second axes when the second and fourth bearing areas are in engagement.

2. The prosthetic joint of claim 1 wherein the convex bearing component comprises the femoral component of an artificial knee joint and wherein said convex bearing component includes a body having an outer surface, said outer surface having first and second portions, the first portion being located anteriorly and the second portion being located distally when the prosthesis is implanted in the femur, the first portion of the outer surface including a surface recess for engagement with a patellar prosthesis, the second portion of the outer surface including a track for engagement with said patellar prosthesis, the track being composed of two rails, the cross-sectional contour of the surface of each of the rails in a direction transverse to the longitudinal axis of the rail being selected from the group consisting of a straight line and a concave curve, said cross-sectional contour being constant along the length of the rail, said rails extending from said surface recess and the cross-sectional contour of the surface of each of said rails being the cross-sectional contour of the surface of the surface recess at the intersection between the rail and the surface recess so that the surface of each rail flows continuously into the surface of the surface recess.

3. The prosthetic joint of claim 2 wherein the cross-sectional contour of each of the rails is concave and is a portion of a circle.

4. The prosthetic joint of claim 2 further including a patellar prosthesis wherein the patellar prosthesis makes contact with each of the rails along a line which is transverse to the longitudinal axis of the rail.

5. The prosthetic joint of claim 3 further including a patellar prosthesis wherein the patellar prosthesis has a saddle-shaped surface and wherein, for at least a portion of the track, the patellar prosthesis makes contact with each of the rails over an area extending along the length of the rail.

6. The prosthetic joint of claim 1 wherein the convex bearing component comprises the femoral component of an artificial knee joint and wherein said convex bearing component includes a body having an outer surface a portion of which is located distally when the prosthesis is implanted in the femur, said portion including a track for engagement with a patellar prosthesis, said track being composed of two rails, the cross-sectional contour of the surface of each of the rails in a direction transverse to the longitudinal axis of the rail being (a) selected from the group consisting of a straight line and a concave curve, and (b) constant along the length of the rail.

7. The prosthetic joint of claim 6 wherein the cross-sectional contour of each of the rails is concave and is a portion of a circle.

8. The prosthetic joint of claim 6 further including a patellar prosthesis wherein the patellar prosthesis makes contact with each of the rails along a line which is transverse to the longitudinal axis of the rail.

9. The prosthetic joint of claim 7 further including a patellar prosthesis wherein the patellar prosthesis has a saddle-shaped surface and wherein, for at least a portion of the track, the patellar prosthesis makes contact with each of the rails over an area extending along the length of the rail.

10. The prosthetic joint of claim 1 wherein the contact area between the convex and concave bearing components is greater when the second and fourth bearing areas are in engagement than when the first and third bearing areas are in engagement.

11. A prosthetic knee joint comprising:
(a) a femoral component having a flexion bearing surface which includes a first bearing area and a contiguous second bearing area, the second bearing area being a surface of revolution about a first axis and having a radius of curvature which is less than the radius of curvature of the first bearing area; and
(b) a tibial component having a flexion bearing surface which includes a third bearing area for engagement during flexion with the first bearing area and a contiguous fourth bearing area for engagement with the second bearing area, the fourth bearing area being a surface of revolution about a second axis and having a radius of curvature which is less than the radius of curvature of the third bearing area;

wherein:
the radius of curvature of the second bearing area of the femoral component is substantially the same as the radius of curvature of the fourth bearing area of the tibial component so that the surface of revolution of the fourth bearing area of the tibial component may be in congruent engagement with the surface of revolution of the second bearing area of the femoral component; and
the flexion axis of the joint is parallel to the first and second axes when the second and fourth bearing areas are in engagement.

12. The prosthetic knee joint of claim 11 wherein the contact area between the flexion bearing surfaces of the femoral and tibial components is greater when the second and fourth bearing areas are in engagement than when the first and third bearing areas are in engagement.

* * * * *